United States Patent

Kojima et al.

[11] Patent Number: 5,147,874
[45] Date of Patent: Sep. 15, 1992

[54] CYCLIC ANTHRANILIC ACID DERIVATIVES AND PROCESS FOR THEIR PREPARATION

[75] Inventors: Eisuke Kojima, Koga; Shizuyoshi Fujimori, Nogi; Katsuya Awano, Oyama, all of Japan

[73] Assignee: Kyorin Pharmaceutical Co., Ltd., Tokyo, Japan

[21] Appl. No.: 560,775

[22] Filed: Jul. 31, 1990

Related U.S. Application Data

[62] Division of Ser. No. 249,996, Sep. 27, 1988, Pat. No. 4,956,372.

[30] Foreign Application Priority Data

Oct. 2, 1987 [JP] Japan .................. 62-249608
Jan. 19, 1988 [JP] Japan .................. 63-8793
Sep. 22, 1988 [JP] Japan .................. 63-236295

[51] Int. Cl.$^5$ .................. A61K 31/395; C07D 265/36
[52] U.S. Cl. .................. 514/238.2; 514/237.8; 514/238.8; 544/105
[58] Field of Search .................. 544/105; 514/237.8, 514/238.2, 238.8

[56] References Cited

PUBLICATIONS

Ono et al. Chem. Abstracts; vol. 111, No. 7; 57743j (1989).

*Primary Examiner*—Johann Richter
*Attorney, Agent, or Firm*—Oblon, Spivak, McClelland, Maier & Neustadt

[57] ABSTRACT

An antirheumatoid pharmaceutical composition containing a cyclic anthranilic acid derivative of the following formula,

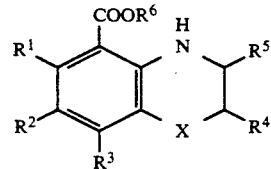

wherein $R^1$, $R^2$ and $R^3$ each independently indicate a hydrogen atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoylmethyl group which may be substituted, methylthio group, phenylethynyl group which may be substituted, ethynyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzyl group; $R^6$ indicates a hydrogen atom, lower alkyl group having 1 to 3 carbon atoms or benzyl group; X is oxygen, sulfur, SO or $SO_2$; the acid or alkali salts thereof and an inert, pharmaceutically acceptable carrier.

2 Claims, No Drawings

CYCLIC ANTHRANILIC ACID DERIVATIVES AND PROCESS FOR THEIR PREPARATION

This is a division of application Ser. No. 07/249,996 filed on Sept. 27, 1988, now U.S. Pat. No. 4,956,372.

DETAILED DESCRIPTION OF THE INVENTION

This invention is concerned with certain novel cyclic anthranilic acid derivatives, their acid and alkali salts thereof and process for their preparation thereof. More particularly, this invention is concerned with the use of these compounds as antirheumatic drugs having immunomodulatory properties.

Moreover, it relates to certain novel cyclic anthranilic acid derivatives of the formula (I),

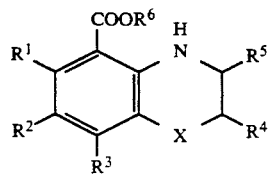
(I)

wherein $R^1$, $R^2$ and $R^3$ each independently indicate a hydrogen atom, halogen atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoylmethyl group which may be substituted, methylthio group, phenylethynyl group which may be substituted, ethynyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzyl group; $R^6$ indicates a hydrogen atom, lower alkyl group having 1 to 3 carbon atoms or benzyl group; X indicates a methylene group, oxygen atom, sulfur atom, sulfinyl group or sulfonyl group; their acid or alkali salts thereof.

Cyclic anthranilic acids that amino groups looped benzene rings have been synthesized by the method oxidizing 1,7-trimethyleneisatins with hydrogen peroxide in aqueous alkali medium (E. Ziegler et al., Monatsh. Chem., 94, 698 (1963), ibid 95, 59 (1964)), and reducing or cyclizing quinoline-8-carboxylic acid (C. Satyendranath et al., J. Annamelai Univ., 2, 227 (1933), L. S. Povarov et al., Izv. Akad. Nauk SSSR. Serkhim, 144 (1966), C. G. Wad et al., J. Heterocycl. Chem., 2, 414 (1965)).

But, all of the literatures have included the very limited compounds and no mentions have been made on pharmacological activity.

The immune-based chronic inflammation triggered by bacteria, viruses or autoantigenes or by an aberration in cytokine regulation of T cells includes rheumatoid arthritis (RA) and other autoimmune diseases such as systemic lupus erythematosus, psoriatic arthritis, atopic dermatitis and ankylosing spondylitis. Especially, patients with RA demonstrate a variety of immunologic abnormalities including reduced functions of suppressor T cells and/or hyperactivity of B cells.

Non-steroidal antiinflammatory drugs are currently the most frequently used 'first-line' therapeutic drugs in the treatment of RA and other diseases due to immunological disorders. While these drugs offer symptomatic relief to patients with these diseases they fail to alter the underlying immunological dysfunction nor overall course of the disease process. Furthermore, serious side effects from prolonged use of these drugs have also been well documented.

On the other hand, disease-modifying antirheumatic drugs such as gold containing compounds and D-penicillamine have little acute antiinflammatory effects but they appear to slow or halt the tissue destruction and more specially the progression of articular damage. They also have the immunomodulatory effects in vivo. So an attempt to modify the immune responses of the host seems a logical therapeutic approach to immune-based chronic inflammation.

As a result of diligent studies about the development of antirheumatoid agent, the inventors have found that novel cyclic anthranilic acid derivatives represented by a general formula (I), their acid or alkali salts thereof, have immunomodulatory activity and high potency for induction of suppressor T cells and have therapeutic effect on RA.

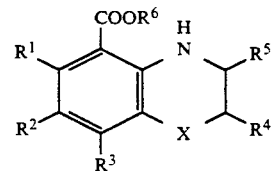
(I)

wherein $R^1$, $R^2$ and $R^3$ each independently indicate a hydrogen atom, halogen atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoylmethyl group which may be substituted, methylthio group, phenylethynyl group which may be substituted, ethynyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzyl group; $R^6$ indicates a hydrogen atom, lower alkyl group having 1 to 3 carbon atoms or benzyl group; X indicates a methylene group, oxygen atom, sulfur atom, sulfinyl group or sulfonyl group.

More specifically in the compounds of formula (I), the term "lower alkyl", as used in the lower alkyl group, lower alkoxy group, lower alkanoylamino group, lower alkylsulfonylamino group and so on, means straight or branched hydrocarbons having 1 to 3 carbon atoms, such as methyl, ethyl, n-propyl or isopropyl group. The term "halogen atom" means fluorine, chlorine, bromine or iodine atom. The term "substituted phenyl" as used in the benzoylmethyl group which may be substituted, phenylsulfonylamino group which may be substituted, benzoylamino group which may be substituted, phenylethynyl group which may be substituted and so on, means phenyl group substituted by 1 to 3 substituents such as, halogen atom, lower alkyl group, lower alkoxy group and hydroxy group.

Accordingly to the invention, the compounds represented by the general formula (I) are prepared by the following routes.

(1) The compounds wherein $R^6$ indicates a hydrogen atom in the general formula (I), namely the compounds represented by the general formula (III) are prepared from the compounds represented by the general formula (II) by treating with alkali solution and then by oxidization. Typically, they can be prepared by the compounds represented by the general formula (II) to hydrolyse with a little excess mole of suitable alkali solution such as, for example, sodium hydroxide or potassium hydroxide, in a suitable solvent such as, for example, water or aqueous alcohol and followed by oxidization with more than equal mole of a mild oxidant such as, for example, hydrogen peroxide solution or acetic peracid. It is desirable that reaction temperature is 0° to 50° C. and reaction time is 0.5 to 3 hours.

When X indicates a sulfur atom in the general formula (II), the compounds wherein X is sulfur atom, sulfinyl or sulfonyl group in the general formula (I) can be prepared predominantly by controlling the amount of oxidant and reaction temperature.

Some compounds in the general formula (II), which are intermediates of this preparation method, have been known publicly as Japan Kokai No. 60-243088 and the others can be prepared easily according to the known method.

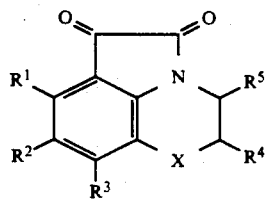
(II)

wherein $R^1$, $R^2$, $R^3$, $R^4$, $R^5$ and X have the same meanings described above.

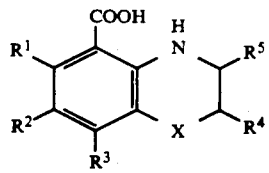
(III)

wherein $R^1$, $R^2$, $R^3$, $R^4$, $R^5$ and X have the same meanings described above.

(2) The compounds wherein $R^6$ indicates a lower alkyl group having 1 to 3 carbon atoms or benzyl group in the general formula (I), namely the compounds represented by the general formula (IV) are prepared from the compounds represented by the general formula (III) by treating with lower alkyl halide or benzyl halide. Typically, they can be prepared from the compounds represented by the general formula (III) by treating with a suitable lower alkyl halide or benzyl halide such as for example, methyl iodide, ethyl iodide or benzyl bromide, in the presence of a suitable base such as, for example, sodium carbonate, potassium carbonate or potassium bicarbonate, in a suitable solvent such as, for example, dimethylformamide, dimethyl sulfoxide, acetone or dioxane at room temperature or in a heated circumstance under stirring.

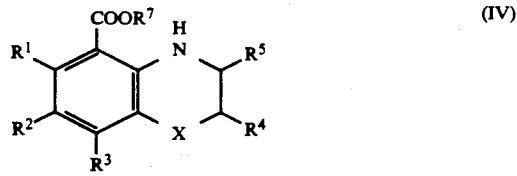
(IV)

wherein $R^1$, $R^2$, $R^3$, $R^4$, $R^5$ and X have the same meanings described above and $R^7$ indicates a lower alkyl group or benzyl group.

(3) The compounds represented by the general formula (III) are also prepared from the compounds represented by the general formula (IV) by hydrolysis or reduction. Typically, when $R^7$ indicates a lower alkyl group, they can be prepared from the compounds represented by the general formula (IV) by hydrolysis with a suitable alkali solution such as, for example, sodium hydroxide or potassium hydroxide, in a suitable solvent such as, for example, methanol or ethanol at room temperature or in a heated circumstance under stirring. When $R^7$ indicates a benzyl group, they can be prepared from the compounds represented by the general formula (IV) by the reduction in the presence of a suitable catalyst such as, for example, 10% palladium on charcoal, in a suitable solvent such as, for example dimethylformamide in the hydrogen atmosphere.

(4) The compounds wherein X indicates sulfur atom in the general formula (I), namely the compounds represented by the general formula (VI) are prepared from the compounds wherein X indicates a sulfinyl or sulfonyl group in the general formula (I), namely the compounds represented by the general formula (V) by the reduction. Typically, they can be prepared from the compounds represented by the general formula (VI) by reduction with a suitable reductant such as, for example, stannous chloride, thitanium trichloride or diphosphorus tetraiodide, according to circumstances, sodium borohydride or lithium aluminum hydride in a suitable solvent such as, for example, methanol, water or dichloromethane at room temperature or in a heated circumstance under stirring.

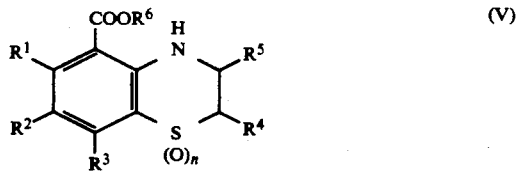
(V)

wherein $R^1$, $R^2$, $R^3$, $R^4$, $R^5$ and $R^6$ have the same meanings described above and n indicates 1 or 2.

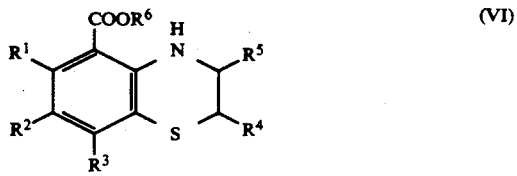
(VI)

wherein $R^1$, $R^2$, $R^3$, $R^4$, $R^5$ and $R^6$ have the same meanings described above.

(5) The compounds represented by the general formula (V) are prepared from the compounds represented by the general formula (VI) by the oxidization. Typically, they can be prepared from the compounds represented by the general formula (V) by the oxidization with equivalent or excess amount of a mild oxidant such as, for example, m-chloroperbenzoic acid, hydrogen peroxide, in a suitable solvent such as, for example, dichloromethane or alcohol at room temperature or in a heated circumstance under stirring.

(6) The compounds wherein X indicates a sulfonyl group in the general formula (I), namely the compounds represented by the general formula (VIII) are prepared from the compounds where X indicates a sulfinyl group in the general formula (I), namely the compounds represented by the general formula (VII) by the oxidization. Typically, they can be prepared from the compounds represented by the general formula (VII) by the oxidization with equivalent or excess amount of a mild oxidant such as, for example, m-chloroperbenzoic acid, hydrogen peroxide, in a suitable solvent such as, for example, dichloromethane or alcohol at room temperature or in a heated circumstance under stirring.

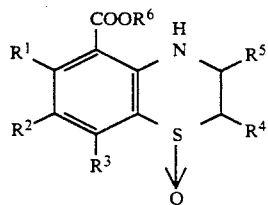

(VII)

wherein $R^1$, $R^2$, $R^3$, $R^4$, $R^5$ and $R^6$ have the same meanings described above.

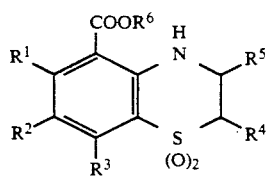

(VIII)

wherein $R^1$, $R^2$, $R^3$, $R^4$, $R^5$ and $R^6$ have the same meanings described above.

(7) The compounds wherein $R^2$ indicates an amino group in the general formula (I), namely the compounds represented by the general formula (IX) are prepared from the compounds wherein $R^2$ indicates a nitro group in the general formula (I), namely the compounds represented by the general formula (X) by the reduction. Typically, they can be prepared from the compounds represented by the general formula (IX) by the reduction in the presence of a suitable catalyst such as, for example, 10% palladium on charcoal, in a suitable solvent such as, for example dimethylformamide in the hydrogen atmosphere.

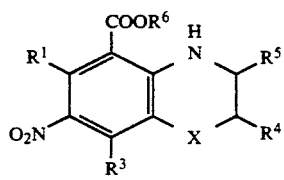

(IX)

wherein $R^1$, $R^3$, $R^4$, $R^5$, $R^6$ and X have the same meanings described above.

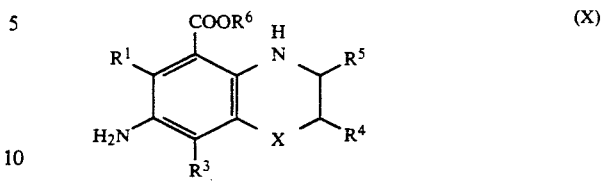

(X)

wherein $R^1$, $R^3$, $R^4$, $R^5$, $R^6$ and X have the same meanings described above.

(8) The compounds of the general formula (I) wherein $R^2$ indicates a lower alkanoylamino group having 1 to 3 carbon atoms, benzoylamino group which may be substituted, lower alkylsulfonylamino group having 1 to 3 carbon atoms or phenylsulfonylamino group which may be substituted, namely the compounds represented by the general formula (XII) are prepared by reacting the compounds of the general formula (I) wherein $R^2$ indicates an amino group, namely the compounds represented by the general formula (X) with the compounds represented by the general formula (XI). Typically, they can be prepared by by reacting the compounds represented by the general formula (X) with the compounds represented by the general formula (XI) in the presence of a suitable base such as, for example, triethylamine or pyridine in a suitable solvent such as, for example, dimethylformamide or dioxane at room temperature under stirring.

$R^8$—Y wherein $R^8$ indicates a lower alkanoyl group having 1 to 3 carbon atoms, benzoyl group which may be substituted, lower alkylsulfonyl group having 1 to 3 carbon atoms or phenylsulfonyl group which may be substituted and Y indicates a halogen atom.

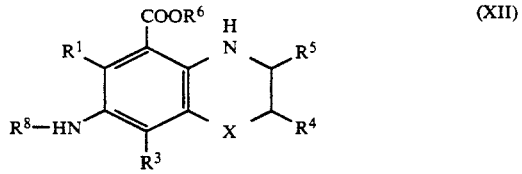

(XII)

wherein $R^1$, $R^3$, $R^4$, $R^5$, $R^6$, $R^8$ and X have the same meanings described above.

(9) The compounds of the general formula (I) wherein $R^2$ indicates a cyano group, namely the compounds represented by the general formula (XIV) are prepared by reacting the compounds of the general formula (I) wherein $R^2$ indicates bromine atom, namely the compounds represented by the general formula (XIII) with cyanogenating agents. Typically, they can be prepared by reacting the compounds represented by the general formula (XIII) with a cyanogenating agent such as, for example, cuprous cyanide, potassium cyanide or sodium cyanide in a suitable solvent such as, for example, dimethylformamide, pyridine or N-methylpyrrolidone in heated circumstance under stirring.

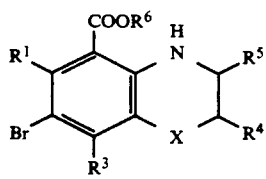

(XIII)

wherein $R^1$, $R^3$, $R^4$, $R^5$, $R^6$ and X have the same meanings described above.

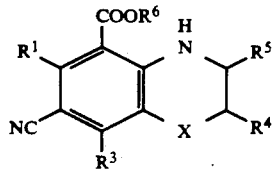

(XIV)

wherein $R^1$, $R^3$, $R^4$, $R^5$, $R^6$ and X have the same meanings described above.

(10) The compounds of the general formula (I) wherein $R^2$ indicates a carbamoyl group or carboxyl group, namely the compounds represented by the general formula (XV) are prepared by hydrolyzing the compounds represented by the general formula (XIV). Typically, they can be prepared by hydrolyzing the compounds represented by the general formula (XIV) in the presence of a suitable base such as, for example, sodium hydroxide or potassium hydroxide in a suitable solvent such as, for example, ethanol or methanol.

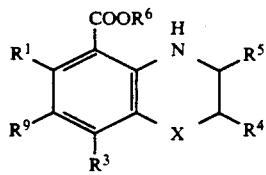

(XV)

wherein $R^1$, $R^3$, $R^4$, $R^5$, $R^6$ and X have the same meanings described above and $R^9$ indicates a carbamoyl group or carboxyl group.

(11) The compounds of the general formula (I) wherein $R^2$ indicates a phenylethynyl group which may be substituted or ethynyl group which may be substituted, namely the compounds represented by the general formula (XVII) are prepared by reacting the compounds of the general formula (I) wherein $R^2$ indicates a iodine atom, namely the compounds represented by the general formula (XVI) with phenylacetylene which may be substituted or acetylene which may be substituted. Typically, they can be prepared by reacting the compounds represented by the general formula (XVII) with phenylacetylene which may be substituted or acetylene which may be substituted in the presence of bis-triphenylphosphine palladium diacetate or bis-triphenylphosphine palladium dichloride and so on, in a suitable solvent such as, for example, dimethylformamide or tetrahydrofuran together with triethylamine and cuprous iodide in a heated circumstance under stirring.

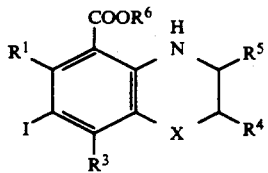

(XVI)

wherein $R^1$, $R^3$, $R^4$, $R^5$, $R^6$ and X have the same meanings described above.

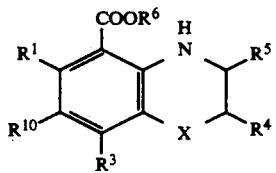

(XVII)

wherein $R^1$, $R^3$, $R^4$, $R^5$, $R^6$ and X have the same meanings described above and $R^{10}$ indicates a phenylethynyl group which may be substituted or ethynyl group which may be substituted.

(12) The compounds of the general formula (I) wherein $R^2$ indicates an acetyl group or benzoylmethyl group, namely the compounds represented by the general formula (XVIII) are prepared by hydrolyzing the compounds represented by the general formula (XVII). Typically, they can be prepared by hydrolyzing the compounds represented by the general formula (XVII) in the presence of a suitable agent such as, for example, concentrated sulfuric acid or mercurous sulfate, in a suitable solvent such as, for example, diluted acetone.

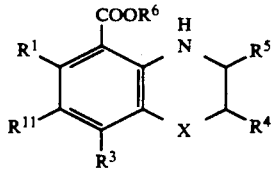

(XVIII)

wherein $R^1$, $R^3$, $R^4$, $R^5$, $R^6$ and X have the same meanings described above and $R^{11}$ indicates an acetyl group or benzoylmethyl group which may be substituted.

Moreover, the compounds represented by the general formula (I) can be converted to the corresponding salts by the treatment with acid or alkali. The acid may be an inorganic acid such as, for example, hydrochloric acid, sulfuric acid or phosphoric acid, or an organic acid such as, for example, methanesulfonic acid, lactic acid, acetic acid, citric acid or tartaric acid. The alkali may be an alkali metal such as, for example, sodium or potassium.

In following, the invention will be illustrated based on concrete examples, but the invention is not confined to these examples.

REFERENCE EXAMPLE 1

5,6-Dihydro-4H-pyrrolo[3,2,1-ij]quinoline-1,2-dione

To the refluxing mixture of oxalyl chloride (22 ml) in dry tetrahydrofuran (THF, 100 ml) was added 1,2,3,4-tetrahydroquinoline (18.5 g) in dry THF (150 ml) dropwise. The mixture was refluxed for 3.5 hours after addition was completed, then cooled to room temperature and concentrated under reduced pressure. The residue was dissolved in carbon disulfide (800 ml) and heated up to reflux. To the refluxing mixture was added aluminum chloride (35 g) portionwise over 5 hours period under stirring. The reaction mixture was refluxed for an additional 3 hours and allowed to stand for overnight at room temperature. After decantation of the solvent, the residue, cooled by an ice bath, was treated with water (150 ml). The mixture was extracted with chloroform and washed with water and dried over anhydrous sodium sulfate. Evaporation of chloroform afforded the title compound. The compound was recrystallized from ethanol to give 21 g (80%) of dark red needles, mp 198°–200° C.

REFERENCE EXAMPLE 2

8-Nitro-5,6-dihydro-4H-pyrrolo[3,2,1-ij]quinoline-1,2-dione

To a stirred fuming nitric acid (20 ml) at 0° C. was added 5,6-dihydro-4H-pyrrolo[3,2,1-ij]quinoline-1,2-dione (5 g) portionwise. The reaction mixture was stirred for additional one hour, poured into ice water and the resultant precipitate was collected by filtration. This precipitate was washed with water and dried to yield the title compound. The compound was recrystallized from ethanol-hexane to give 3.8 g (61%) as yellow needles, mp 198°–199° C.

REFERENCE EXAMPLE 3

8-Nitro-2,3-dihydropyrrolo[1,2,3-de]-1,4-benzoxazine-5,6-dione dione

To a stirred solution of 2,3-dihydropyrrolo[1,2,3-de]-1,4-benzoxazine-5,6-dione (33.1 g) in acetic acid-acetic anhydride (200 ml, 1:1) under ice-cooling was added fuming nitric acid (9.4 ml) dropwise. The mixture was stirred for 0.5 hours at the same temperature (0° C.) and for an hour at room temperature. The reaction mixture was poured into ice water (500 ml) and the resultant precipitate was collected by filtration. This precipitate was washed with water and dried to give 26.9 g (65.5%) of the title compound. The filtrate was extracted with chloroform, washed with water, saturated aqueous sodium bicarbonate, water and saturated aqueous sodium chloride solution successively and then dried over anhydrous sodium sulfate. Evaporation of chloroform further afforded 2.9 g of the title compound. This compound was recrystallized from acetonitrile to give yellow needles, mp 230°–232° C.

REFERENCE EXAMPLE 4

3-Phenyl-2,3-dihydropyrrolo1,2,3-de]-1,4-benzoxazine-5,6-dione (a)
3,4-Dihydro-3-phenyl-2H-1,4-benzoxazinecarbonylmethylpyridinium chloride Chloroacetyl chloride (8.36 g) in dry benzene (50 ml) was added dropwise to a stirred and ice cooled solution of 3,4-dihydro-3-phenyl-2H-1,4-benzoxazine (15.6 g) in dry benzene (250 ml) containing of pyridine (5.85 g), and then stirred at room temperature for 3 hours. The reaction mixture was treated with water (300 ml) to dissolve precipitated salts, extracted with benzene, washed with water and saturated aqueous sodium chloride solution successively and dried over anhydrous sodium sulfate. Evaporation of benzene afforded 21.3 g (quant.) of 1-chloroacetyl-3,4-dihydro-3-phenyl-2H-1,4-benzoxazine. This compound was recrystallized from ethanol to give colorless needles, mp 131°–132° C.

The mixture of above chloroacetyl derivatives and pyridine (150 ml) was refluxed for 10 minutes and then cooled to room temperature and triturated with benzene. After decantation of the solvent, the residue was treated with acetone and resultant precipitate was collected by filtration, washed with acetone and dried to give 27.1 g (70%) of the title compound.

(b)
3,4-Dihydro-1-[2-(p-dimethylaminophenyl)iminoacetyl]-3-phenyl-2H-1,4-benzoxazine N'-oxide A solution of p-nitroso-N,N-dimethylaniline (4.8 g) in dimethylformamide (DMF, 50 ml) was added to the above pyridinium chloride derivative (11.9 g) in water (50 ml). The mixture was cooled to 0° C., and 2N sodium hydroxide solution (16 ml) was added dropwise with vigorous stirring and the stirring was continued for 2 hours at room temperature. Then water (300 ml) was added dropwise with vigorous stirring to form a precipitate, collected by filtration, washed with water and dried to yield 5.5 g (42.8%) of the title compound as yellowish green powder. The compound was recrystallized from acetonitrile to give yellowish green crystals, mp 180°–183° C.

(c)
3-Phenyl-2,3-dihydropyrrolo[1,2,3-de]-1,4-benzoxazine-5,6-dione

The above product (5.5 g) was added portionwise with stirring to concentrated hydrochloric acid (40 ml) in an ice bath. The mixture was stirred for an hour and allowed to stand for overnight and poured into water (40 ml). The red precipitate was collected by filtration, washed with water and dried to yield 3.5 g (96.3%) of the title compound. The compound was recrystallized from isopropanol to give dark red needles, mp 169°–171° C.

REFERENCE EXAMPLE 5

2-Phenyl-2,3-dihydropyrrolo[1,2,3-de]-1,4-benzoxazine-5,6-dione

The procedure described in Reference example 4 was repeated using 3,4-dihydro-2-phenyl-2H-1,4-benzoxazine as starting material. The title compound was obtained in 58.3% of overall yield.

REFERENCE EXAMPLES 6–10

Using the procedure described in Reference examples 1 to 4, the compounds described in Reference examples 6 to 10 shown in Table 1 have been obtained.

TABLE 1

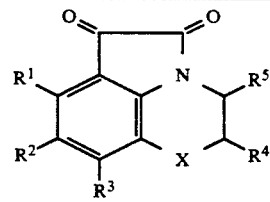

| Reference example | X | R¹ | R² | R³ | R⁴ | R⁵ | Yield (%) | mp (°C.)* |
|---|---|---|---|---|---|---|---|---|
| 6 | CH$_2$ | H | NO$_2$ | H | H | CH$_3$ | 91.5 | 158–160 (A) |
| 7 | CH$_2$ | H | H | H | H | Ph | 78.3 | 129–130 (B) |
| 8 | O | Cl | H | H | H | H | 66.5 | 232 (B) |
| 9 | O | H | NO$_2$ | Cl | H | H | 86.5 | 259–260 (B) |

TABLE 1-continued

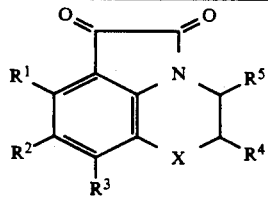

| Reference example | X | R¹ | R² | R³ | R⁴ | R⁵ | Yield (%) | mp (°C.)* |
|---|---|---|---|---|---|---|---|---|
| 10 | S | H | H | Cl | H | H | 77.5 | 217-219 (B) |

*: recryst. solvent,
A: ethanol,
B: acetonitrile

REFERENCE EXAMPLE 11

8-Bromo-5,6-dihydro-4H-pyrrolo[3,2,1-ij]quinoline-1,2-dione

A mixture of 5,6-dihydro-4H-pyrrolo[3,2,1-ij]quinoline-1,2-dione (10 g) and N-bromosuccinimide (10 g) in DMF (60 ml) was stirred at 70° C. for 5 hours. After cooling, to the mixture was added ethyl acetate (500 ml) and washed with water and saturated aqueous sodium chloride solution successively, and then dried over anhydrous sodium sulfate. Evaporation of ethyl acetate afforded the title compound The compound was recrystallized from ethanol to give 14 g (98.4%) as dark red needles.

REFERENCE EXAMPLE 12

5,6-Dihydro-8-iodo-4H-pyrrolo[3,2,1-ij]quinoline-1,2-dione

A mixture of 5,6-dihydro-4H-pyrrolo[3,2,1-ij]quinoline-1,2-dione (5 g) and iodine monochloride (5 g) in acetic acid (30 ml) was refluxed for 5 hours. After cooling, the mixture was poured into ice water and extracted with chloroform. The extract was washed with water, saturated aqueous sodium bicarbonate solution and saturated aqueous sodium chloride solution successively and then dried over anhydrous sodium sulfate. Evaporation of chloroform afforded the title compound. The compound was recrystallized from ethanol to give 6.2 g (73.8%) as dark red needles.

REFERENCE EXAMPLE 13

8-Bromo-2,3-dihydropyrrolo[1,2,3-de]-1,4-benzothiazine-5,6-dione

To a solution of 2,3-dihydropyrrolo[1,2,3-de]-1,4-benzothiazine-5,6-dione (2.05 g) in acetic acid (40 ml) was added bromine (0.5 ml) in acetic acid (10 ml) dropwise. The mixture was stirred for 5 hours at room temperature and poured into ice water (200 ml) and the resultant precipitate was collected by filtration, washed with water and dried to yield the title compound (2.10 g, 73.9%). The compound was recrystallized from acetonitrile to give dark red needles, mp 196° C.

EXAMPLE 1

7-Chloro-3,4-dihydro-2H-1,4-benzoxazine-5-carboxylic acid

To a stirred suspension of 8-chloro-2,3-dihydropyrrolo[1,2,3-de]-1,4-benzoxazine-5,6-dione (4.47 g) in water (50 ml) was added 2N sodium hydroxide solution (30 ml), and the mixture was stirred to a solution. 30 % hydrogen peroxide solution (20 ml) was added and stirred for an hour, insoluble material was filtered off and then acidified with concentrated hydrochloric acid. The yellow precipitate was collected by filtration, washed with water and dried to yield 3.44 g (80.5%) of the title compound. The compound was recrystallized from benzene (75 ml) to give pale yellow prisms, mp 209°-210° C.

Analysis (%) for $C_9H_8ClNO_3$, Calcd. (Found): C, 50.60 (50.73); H, 3.77. (3.73); N, 6.56 (6.50).

EXAMPLE 2

7-Bromo-3,4-dihydro-2H-1,4-benzothiazine-5-carboxylic acid

To a suspension of 8-bromo-2,3-dihydropyrrolo[1,2,3-de]-1,4-benzothiazine-5,6-dione (4.6 g) in water (50 ml) was added 2N sodium hydroxide solution (30 ml) and dissolved. To the solution was added 30% hydrogen peroxide solution (4 ml) at 15° C. After stirring for 30 minutes, the mixture was brought to slightly acidic by the addition of concentrated hydrochloric acid. The resulting crystals were collected by filtration, washed with water and dried to give the title compound (4.1 g, 92.3%) which was recrystallized from ethanol as pale yellow needles, mp 205°-206° C. (decompd.).

Analysis (%) for $C_9H_8BrNO_2S$, Calcd. (Found): C, 39.43 (39.31); H, 2.94 (2.87); N, 5.11 (5.10).

EXAMPLE 3

7-Bromo-3,4-dihydro-2H-1,4-benzothiazine-5-carboxylic acid-1,1-dioxide

To a suspension of 8-bromo-2,3-dihydropyrrolo[1,2,3-de]-1,4-benzothiazine-5,6-dione (6 g) in water (50 ml) was added 2N sodium hydroxide solution (30 ml) and dissolved. To this solution was added 35% hydrogen peroxide solution (20 ml) and the mixture was stirred for an hour without cooling. The mixture was brought to slightly acidic by the addition of concentrated hydrochloric acid. The resulting precipitate was collected by filtration, washed with water and dried to give the title compound (5.80 g, 90.3%) which was recrystallized from ethanol to give colorless crystals, mp 250°-251° C. (decompd.).

Analysis (%) for $C_9H_8BrNO_4S$, Calcd. (Found): C, 35.31 (35.21); H, 2.63 (2.62); N, 4.58 (4.71).

EXAMPLE 4

7-Bromo-3,4-dihydro-2H-1,4-benzothiazine-5-carboxylic acid-1-oxide

To a solution of 7-bromo-3,4-dihydro-2H-1,4-benzothiazine-5-carboxylic acid (500 mg) in methanol 80 ml) was added 0.05M sodium metaperiodate solution (40 ml) The mixture was stirred for 5 hours at room temperature, then diluted with water (500 ml) and concentrated until crystals began to separate. The crystals were collected and dried to give the title compound (300 mg, 57.5% which was recrystallized from ethanol to give pale yellow crystals, mp 254°-255° C. (decompd.).

Analysis (%) for $C_9H_8BrNO_3S$, Calcd. (Found): C, 37.26 (37.29); H, 2.78 (2.66); N, 4.83 (4.82).

EXAMPLES 5-30

Using the procedure described in Examples 1-4, the compounds described in Examples 5-30 shown in Table 2-3 have been obtained.

TABLE 2

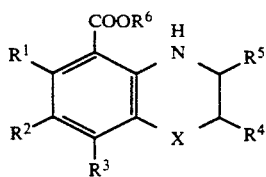

| Example | X | R¹ | R² | R³ | R⁴ | R⁵ | R⁶ | Yield (%) | mp (°C.)* | Analysis Calcd. (%) Found C | H | N |
|---|---|---|---|---|---|---|---|---|---|---|---|---|
| 5 | O | H | F | Cl | H | H | H | 86.5 | 213–234 (A) | 46.67 | 3.05 | 6.05 |
|   |   |   |   |   |   |   |   |      |             | 46.73 | 3.04 | 6.10 |
| 6 | O | H | CH₃ | H | H | H | H | 39.3 | 197–197.5 (A) | 62.16 | 5.74 | 7.25 |
|   |   |   |   |   |   |   |   |      |             | 62.18 | 5.68 | 7.17 |
| 7 | O | H | H | H | H | H | H | 81.5 | 185.5–186 (B) | 60.33 | 5.06 | 7.82 |
|   |   |   |   |   |   |   |   |      |             | 60.36 | 5.01 | 7.80 |
| 8 | O | H | H | Cl | H | H | H | 84.8 | 225–226 (A) | 50.60 | 3.77 | 6.56 |
|   |   |   |   |   |   |   |   |      |             | 50.52 | 3.68 | 6.53 |
| 9 | O | H | Br | Cl | H | H | H | 49.1 | 233–235 (A) | 36.95 | 2.41 | 4.79 |
|   |   |   |   |   |   |   |   |      |             | 37.40 | 2.41 | 5.05 |
| 10 | O | Cl | H | H | H | H | H | 60.0 | 156 (A) | 50.60 | 3.77 | 6.56 |
|   |   |   |   |   |   |   |   |      |             | 50.53 | 3.71 | 6.56 |
| 11 | SO | H | H | Cl | H | H | H | 76.0 | 257 (A) | 44.00 | 3.28 | 5.70 |
|   |   |   |   |   |   |   |   |      |             | 44.05 | 3.18 | 5.67 |
| 12 | O | H | NO₂ | H | H | H | H | 73.0 | 270 (dec) (A) | 48.22 | 3.60 | 12.50 |
|   |   |   |   |   |   |   |   |      |             | 48.30 | 3.57 | 12.56 |
| 13 | O | H | H | H | H | Ph | H | 74.1 | 196–197 (A) | 70.58 | 5.13 | 5.49 |
|   |   |   |   |   |   |   |   |      |             | 70.41 | 5.11 | 5.46 |
| 14 | O | H | F | H | H | H | H | 29.2 | 178 (A) | 54.83 | 4.09 | 7.10 |
|   |   |   |   |   |   |   |   |      |             | 54.58 | 3.99 | 7.00 |
| 15 | O | H | NO₂ | Cl | H | H | H | 98.6 | 295 (C) | 41.80 | 2.73 | 10.83 |
|   |   |   |   |   |   |   |   |      |             | 41.71 | 2.74 | 10.81 |

*: recryst. solvent.
A: ethanol.
B: benzene.
C: acetonitrile

TABLE 3

| Example | X | R¹ | R² | R³ | R⁴ | R⁵ | R⁶ | Yield (%) | mp (°C.)* | Analysis Calcd. (%) Found C | H | N |
|---|---|---|---|---|---|---|---|---|---|---|---|---|
| 16 | O | H | OMe | H | H | H | H | 61.7 | 164 (A) | 57.41 | 5.30 | 6.70 |
|   |   |   |   |   |   |   |   |      |         | 57.29 | 5.27 | 6.65 |
| 17 | O | H | H | H | Ph | H | H | 36.6 | 215 (A) | 70.58 | 5.13 | 5.49 |
|   |   |   |   |   |   |   |   |      |         | 70.59 | 5.10 | 5.51 |
| 18 | CH₂ | H | NO₂ | H | H | H | H | 80 | 256–258 (A) | 54.05 | 4.54 | 12.61 |
|   |   |   |   |   |   |   |   |      |             | 54.11 | 4.55 | 12.70 |
| 19 | CH₂ | H | Cl | H | H | H | H | 61.4 | 213–215 (A) | 56.74 | 4.76 | 6.62 |
|   |   |   |   |   |   |   |   |      |             | 56.74 | 4.71 | 6.60 |
| 20 | CH₂ | H | Br | H | H | H | H | 71.6 | 200–201 (A) | 46.90 | 3.94 | 5.47 |
|   |   |   |   |   |   |   |   |      |             | 46.90 | 3.87 | 5.42 |
| 21 | CH₂ | H | I | H | H | H | H | 47.3 | 181–182 (A) | 39.63 | 3.33 | 4.62 |
|   |   |   |   |   |   |   |   |      |             | 39.74 | 3.29 | 4.61 |
| 22 | CH₂ | H | Cl | H | H | CH₃ | H | 44.8 | 240–241 (A) | 58.54 | 5.36 | 6.21 |
|   |   |   |   |   |   |   |   |      |             | 58.69 | 5.31 | 6.22 |
| 23 | CH₂ | H | H | H | H | H | H | 58 | 165–167 (A) | 67.78 | 6.26 | 7.91 |
|   |   |   |   |   |   |   |   |      |             | 67.39 | 6.25 | 7.81 |
| 24 | CH₂ | H | NO₂ | H | H | CH₃ | H | 41.7 | 269–272 (A) | 55.93 | 5.12 | 11.86 |
|   |   |   |   |   |   |   |   |      |             | 55.57 | 5.10 | 11.81 |
| 25 | CH₂ | H | H | H | H | Ph | H | 92.6 | 190 (A) | 75.87 | 5.97 | 5.54 |
|   |   |   |   |   |   |   |   |      |         | 75.52 | 5.93 | 5.43 |
| 26 | S | H | H | H | H | H | H | 67.1 | 187 (A) | 55.37 | 4.64 | 7.17 |
|   |   |   |   |   |   |   |   |      |         | 55.13 | 4.55 | 7.19 |
| 27 | SO₂ | H | H | H | H | H | H | 92.6 | 274 (A) | 47.57 | 3.99 | 6.16 |
|   |   |   |   |   |   |   |   |      |         | 47.50 | 3.92 | 6.13 |
| 28 | S | H | Cl | H | H | H | H | 65.2 | 215 (A) | 47.06 | 3.51 | 6.10 |
|   |   |   |   |   |   |   |   |      |         | 47.11 | 3.58 | 6.12 |
| 29 | SO₂ | H | Cl | H | H | H | H | 56.2 | 287 (A) | 41.31 | 3.08 | 5.15 |
|   |   |   |   |   |   |   |   |      |         | 41.38 | 3.07 | 5.39 |

*: recryst. solvent, A: ethanol, B: benzene, C: acetonitrile

TABLE 4

| Example | X | R¹ | R² | R³ | R⁴ | R⁵ | R⁶ | Yield (%) | mp (°C).* | Analysis Calcd. (%) Found | | |
|---|---|---|---|---|---|---|---|---|---|---|---|---|
| | | | | | | | | | | C | H | N |
| 30 | $CH_2$ | H | $NO_2$ | H | H | Ph | H | 72.4 | 253–255 (A) | 64.42 | 4.73 | 9.39 |
| | | | | | | | | | | 64.65 | 4.78 | 9.28 |

*: recryst. solvent, A: ethanol, B: benzene, C: acetonitrile

EXAMPLE 31

6-Amino-1,2,3,4-tetrahydroquinoline-8-carboxylic acid

A solution of 6-nitro-1,2,3,4-tetrahydroquinoline-8-carboxylic acid (4.5 g) in DMF (200 ml) was hydrogenated in the presence of 10% palladium on charcoal (1 g) for 5 hours. After removal of the catalyst by filtration, solvent was distilled away to give the title compound (3.72 g, 96.8%). This compound was recrystallized from DMF-ethanol to give brown crystals, mp 207°–208° C.

Analysis (%) for $C_{10}H_{12}N_2O_2$, Calcd. (Found): C, 62.49 (62.07); H, 6.29 (6.33); N, 14.57 (14.45).

EXAMPLE 32

6-p-Toluenesulfonylamino-1,2,3,4-tetrahydroquinoline-8-carboxylic acid (a) Methyl 6-amino-1,2,3,4-tetrahydroquinoline-8-carboxylate A solution of 6-nitro-1,2,3,4-tetrahydroquinoline-8-carboxylic acid (9.5 g) in DMF (200 ml) was added methyl iodide (6.6 ml) and potassium carbonate (17.83 g), the mixture was stirred for an hour at room temperature. After removal of insoluble material, solvent was distilled away. The resulting residue was dissolved in ethyl acetate (500 ml), washed with water and saturated sodium chloride solution successively and dried over anhydrous sodium sulfate. Solvent was distilled away to yield 9.72 g (96.4%) of ester compound. This compound was treated by the same procedure as in example 31 to give the title compound (92%) as brown crystals.

(b) 6-p-Toluenesulfonylamino-1,2,3,4-tetrahydroquinoline-8-carboxylic acid

A solution of methyl 6-amino-1,2,3,4-tetrahydroquinoline-8-carboxylate (4.12 g) in dioxane (200 ml) was added triethylamine (1.7 ml) and p-toluenesulfonyl chloride (4.57 g), the mixture was stirred for 2 hours at room temperature. Water (500 ml) was added and extracted with ethyl acetate (600 ml 2), washed with saturated aqueous sodium chloride solution and dried over anhydrous sodium sulfate. After solvent was distilled away, the resulting residue was purified by silica gel column chromatography eluting with ethyl acetate-n-hexane (1:2) to give 6.47 g (89.8 %) of yellow crystals.

This compound (6.47 g) was refluxed in ethanol (200 ml) and 1N sodium hydroxide solution (54 ml) for 3 hours. After cooling, water (300 ml) was added and then concentrated hydrochloric acid was added to acidify. The resulting crystals were collected by filtration, washed with water and dried to give 5.79 g (93.0%) of the title compound which was recrystallized from ethanol to give white crystals, mp 251° C.

Analysis (%) for $C_{17}H_{18}N_2O_4S$, Calcd. (Found): C, 58.94 (58.92); H, 5.24 (5.16); N, 8.09 (8.04).

EXAMPLE 33

6-Methanesulfonylamino-1,2,3,4-tetrahydroquinoline-8-carboxylic acid

The title compound was prepared (79.9% yield) from methyl 6-amino-1,2,3,4-tetrahydroquinoline-8-carboxylate by the same procedure as in Example 32 by using methanesulfonyl chloride instead of p-toluenesulfonyl chloride. This compound was recrystallized form ethanol to give yellow crystals, mp 244° C.

Analysis (%) for $C_{11}H_{14}N_2O_4S$, Calcd. (Found): C, 48.88 (48.88); H, 5,22 (5.29); N, 10.36 (10.28).

EXAMPLE 34

6-acetylamino-1,2,3,4-tetrahydroquinoline-8-carboxylic acid

A solution of 6-amino-1,2,3,4-tetrahydroquinoline-8-carboxylic acid (4.80 g) in dioxane (60 ml) was added 1N aqueous sodium hydroxide solution (60 ml) and acetyl chloride (2.5 ml), the mixture was stirred for 8 hours at room temperature. After salting out, extracted with ethyl acetate, washed with water and saturated aqueous sodium chloride solution successively and dried over anhydrous sodium sulfate. After solvent was distilled away and the resulting residue was purified by silica gel column chromatography eluting with dichloromethane-ethanol (9:1) to yield 0.98 g (16.8%) of the title compound. This compound was recrystallized from ethanol to give yellow crystals, mp 258°–259° C.

Analysis (%) for $C_{12}H_{14}N_2O_3$, Calcd. (Found): C, 61.53 (61.38); H, 6.02 (6.02); N, 11.96 (11.92).

EXAMPLE 35

3,4-Dihydro-7-p-toluenesulfonylamino-2H-1,4-benzoxazine-5-carboxylic acid

The title compound was prepared (5.3% yield) from 3,4-dihydro-7-nitro-2H-1,4-benzoxazine-5-carboxylic acid by the same procedure as in Examples 31 and 32 (b). This compound was recrystallized form ethanol to give colorless crystals, mp 213°–215° C.

Analysis (%) for $C_{16}H_{16}N_2O_5S$, Calcd. (Found): C, 55.16 (54.87); H, 4.63 (4.88); N, 8.04 (7.75).

EXAMPLE 36

7-Acetylamino-3,4-dihydro-2H-1,4-benzoxazine-5-carboxylic acid

The title compound was prepared (17.8% yield) from 3,4-dihydro-7-nitro-2H-1,4-benzoxazine-5-carboxylic acid by the same procedure as in Examples 31 and 34. This compound was recrystallized form ethanol to give yellow crystals, mp 253° C.

Analysis (%) for $C_{11}H_{12}N_2O_4S$, Calcd. (Found): C, 55.93 (55.86); H, 5.12 (5.06); N, 11.86 (11.84).

EXAMPLE 37

6-Cyano-1,2,3,4-tetrahydroquinoline-8-carboxylic acid (a) Benzyl 6-cyano-1,2,3,4-tetrahydroquinoline-8-carboxylate To a solution of 6-bromo-1,2,3,4-tetrahydroquinoline-8-carboxylic acid (4.91 g) in DMF (80 ml) was added benzyl bromide (2.5 ml) and potassium carbonate (7.88 g). The reaction mixture was stirred at room temperature for an hour, and then insoluble material was filtered off. To this filtrate was added ethyl acetate-n-hexane (1:1, 400 ml), washed with water, aqueous saturated sodium chloride solution successively and dried over anhydrous sodium sulfate. The solvent was evaporated to give the title compound (6.71 g, quant.).

The above ester (6.71 g) was dissolved in DMF (20 ml) and cuprous cyanide (2.27 g) was added to this solution. The reaction mixture was refluxed for 20 hours. The reaction mixture was poured into the solution of ferric chloride hexahydrate (8 g) in concentrated hydrochloric acid (2 ml)-water (100 ml), and then stirred at 60° C for 0.5 hours. The mixture was extracted with ethyl acetate-benzene (1:1), the organic layer was washed with water, 6N hydrochloric acid, water, aqueous 10% sodium hydroxide solution, water, saturated aqueous sodium chloride solution successively, dried over anhydrous sodium sulfate and evaporated. The residue was purified by silica gel column chromatography eluting with ethyl acetate-n-hexane (1:3) to give the title compound (4.31 g, 77.6%).

(b) 6-cyano-1,2,3,4-tetrahydroquinoline-8-carboxylic acid

The above ester was reacted in a similar manner as Example 31 to give the title compound (89.2%). This compound was recrystallized from ethanol to give yellow needles, mp 238° C.

Analysis (%) for $C_{11}H_{10}N_2O_2$, Calcd. (Found): C, 65.34 (65.17); H, 4.98 (4.96); N, 13.85 (13.68).

EXAMPLE 38

6-Carbamoyl-1,2,3,4-tetrahydroquinoline-8-carboxylic acid

To the solution of benzyl 6-cyano-1,2,3,4-tetrahydroquinoline-8-carboxylate (2.5 g) in ethanol (20 ml) was added 35% hydrogen peroxide solution (3 ml) and 6N sodium hydroxide solution (0.33 ml). The reaction mixture was stirred at 40°-45° C. for 7 hours. The resulting precipitate was collected by filtration and washed with ethanol to give benzyl 6-carbamoyl-1,2,3,4-tetrahydroquinoline-8-carboxylate (1.10 g, 41.7%).

This ester was converted to the title compound (quant.) in the same manner as Example 31. This compound was recrystallized from DMF-ethanol to give pale yellow crystals, mp 268°-269° C.

Analysis (%) for $C_{11}H_{12}N_2O_3$, Calcd. (Found): C, 59.99 (59.56); H, 5.49 (5.47); N, 12.72 (12.54).

EXAMPLE 39

1,2,3,4-Tetrahydroquinoline-6,8-dicarboxylic acid

To a solution of benzyl 6-cyano-1,2,3,4-tetrahydroquinoline-8-carboxylate (2.0 g) in ethanol (20 ml) was added 1N sodium hydroxide solution (30 ml) and the mixture was refluxed for 10 hours. The reaction mixture was acidified with concentrated hydrochloric acid. The resulting precipitate was collected by filtration, washed with water and dried to give the title compound (1.47 g, 98%). This compound was recrystallized from DMF-ethanol to give yellow crystals, mp 298°-299° C.

Analysis (%) for $C_{11}H_{11}NO_4$, Calcd. (Found): C, 59.73 (59.49); H, 5.01 (4.94); N, 6.33 (6.29).

EXAMPLE 40

7-Cyano-3,4-dihydro-2H-1,4-benzothiazine-5-carboxylic acid

The title compound was prepared (7.8% yield) from 7-bromo-3,4-dihydro-2H-1,4-benzothiazine-5-carboxylic acid by the same procedure as in Example 37. This compound was recrystallized from ethanol to give yellow needles, mp 241°-242° C.

Analysis (%) for $C_{10}H_8N_2O_2S$, Calcd. (Found): C, 54.53 (54.47); H, 3.66 (3.70); N, 12.72 (12.53).

EXAMPLE 41

3,4-Dihydro-2H-1,4-benzothiazine-5,7-dicarboxylic acid

The title compound was prepared (72.2% yield) from benzyl 7-cyano-3,4-dihydro-2H-1,4-benzothiazine-5-carboxylate by the same procedure as in Example 39. This compound was recrystallized form DMF-ethanol to give yellow crystals, mp >300° C.

Analysis (%) for $C_{10}H_9NO_4S$, Calcd. (Found): C, 50.20 (50.13); H, 3.79 (3.85); N, 5.85 (5.87).

EXAMPLE 42

3,4-Dihydro-2H-1,4-benzothiazine-5,7-dicarboxylic acid-1-oxide

Benzyl 7-cyano-3,4-dihydro-2H-1,4-benzothiazine-5-carboxylate-1-oxide was prepared (88.9% yield) from benzyl 7-cyano-3,4-dihydro-2H-1,4-benzothiazine-5-carboxylate by the same procedure as in Example 4. The title compound was prepared (81.7% yield) from above ester by the same procedure as in Example 41. This compound was recrystallized form DMF-ethanol to give colorless needles, mp >300° C.

Analysis (%) for $C_{10}H_9NO_5S$, Calcd. (Found): C, 47.06 (46.84); H, 3.55 (3.58); N, 5.49 (5.58).

EXAMPLE 43

6-(2-Phenylethynyl)-1,2,3,4-tetrahydroquinoline-8-carboxylic acid

Methyl 6-iodo-1,2,3,4-tetrahydroquinoline-8-carboxylate was prepared (quant.) in a similar manner to Example 32 (a) from 6-iodo-1,2,3,4-tetrahydroquinoline-8-carboxylic acid. To a mixture of this ester (2 g), bis-triphenylphosphine palladium dichloride (440 mg) and cuprous iodide (120 mg) in DMF (80 ml) was added triethylamine (7 ml) and phenylacetylene (780 mg). The reaction mixture was stirred at 80° C. for 10 hours and then evaporated. The resulting residue was purified by silica gel column chromatography eluting with ethyl acetate-n-hexane (1:7) to give methyl 6-(2-phenylethynyl)-1,2,3,4-tetrahydroquinoline-8-carboxylate.

To a solution of this ester in ethanol (30 ml) was added 1N sodium hydroxide solution (10 ml). The reaction mixture was refluxed for 5 hours and then acidified with concentrated hydrochloric acid. The resulting precipitate was collected by filtration, washed with water and dried to give the title compound (510 mg, 29.2%). This compound was recrystallized from ethanol to give yellow crystals, mp 187°–188° C.

Analysis (%) for $C_{18}H_{15}NO_2$, Calcd. (Found): C, 77.96 (78.19); H, 5.45 (5.50); N, 5.05 (5.01).

EXAMPLE 44

6-Acetyl-1,2,3,4-tetrahydroquinoline-8-carboxylic acid

Methyl 6-(2-trimethylsilylethynyl-1,2,3,4-tetrahydroquinoline-8-carboxylate was prepared (84.6%) in a similar manner to Example 43 from 6-iodo-1,2,3,4-tetrahydroquinoline-8-carboxylic acid. To this compound (6.52 g) in THF (100 ml) was added tetra(n-butyl)ammonium fluoride (8.59 g) and stirred at room temperature under argon atmosphere for 17 hours. Water (200 ml) was added, and the mixture was extracted with ethyl acetate. The organic layer was washed with saturated aqueous sodium chloride solution, dried over anhydrous sodium sulfate and concentrated under reduced pressure. The resulting residue was purified by silica gel column chromatography eluting with ethyl acetate-n-hexane (1:4) to give yellow crystals (3.76 g).

A mixture of this compound (2.26 g) in 70% diluted acetone (75 ml) was added concentrated sulfuric acid (7.7 g) and mercuric sulfate (3.11 g) and the mixture was refluxed for 10 hours. After the mixture was cooled with water, water (300 ml) was added, then the mixture was neutralized with sodium carbonate and extracted with ethyl acetate. The organic layer was washed with water and saturated aqueous sodium chloride solution successively, dried over anhydrous sodium sulfate and concentrated under reduced pressure. The resulting residue was purified by silica gel column chromatography eluting with ethyl acetate-n-hexane (1:7) to give methyl 6-acetyl-1,2,3,4-tetrahydroquinoline-8-carboxylate (2.04 g, 83.8%).

A mixture of this ester (2.04 g) in ethanol (30 ml) and 1N aqueous sodium hydroxide solution (20 ml) was refluxed for 3.5 hours. To the reaction mixture was added water (150 ml) and then the mixture was acidified with concentrated hydrochloric acid. The precipitate was collected by filtration and washed with water and dried to give the title compound (1.83 g, 96%). This compound was recrystallized from ethanol to give yellow needles, mp 229° C.

Analysis (%) for $C_{12}H_{13}NO_3$, Calcd. (Found): C, 65.74 (65.49); H, 5.98 (6.00); N, 6.39 (6.30).

EXAMPLE 45

8-Chloro-3,4-dihydro-2H-1,4-benzothiazine-5-carboxylic acid

A mixture of 8-chloro-3,4-dihydro-2H-1,4-benzothiazine-5-carboxylic acid-1-oxide (2.5 g) and stannous chloride dihydrate (4.51 g) in methanol (20 ml) was refluxed for 21 hours. To the reaction mixture was added ethyl acetate (200 ml), washed with water and dried over anhydrous sodium sulfate. After concentrated under reduced pressure, the resulting residue was purified by silica gel column chromatography eluting with dichloromethaneethanol (9:1) to give the title compound (450 mg, 19.6%). This compound was recrystallized from ethanol to give yellow needles, mp 220° C.

Analysis (%) for $C_9H_8ClNO_2S$, Calcd. (Found): C, 47.06 (47.12); H, 3.51 (3.50); N, 6.10 (6.09).

The following Experiments indicate that the compounds of this invention have immunomodulatory and antiinflammatory properties in vivo and further support the potential use of immunomodulatory and disease-modifying drugs in RA and other autoimmune diseases.

EXPERIMENT 1

Augmentation of antibody response to sheep red blood cells (SRBC)

Mice (BALB/c strain, male) were immunized intravenously with $1 \times 10^7$ SRBC. Two days later, anti SRBC-antibody-producing cells in the spleen were assayed as plague forming cells (PFC) by hemolytic plague assay (A. J. Cunningham and A. Szenberg, Immunology 14, 599, 1968). The compounds of this invention were suspended in 0.3% carboxymethyl cellulose (CMC) and orally administered immediately after antigen injection.

As shown in Table 5, administration of the compounds of this invention significantly augmented antibody response to SRBC when mice were immunized with suboptimal dose of antigen.

TABLE 5

| Compound | Dose (mg/kg) | PFC/spleen (Mean ± S.E.) |
|---|---|---|
| Control | — | 480 ± 48 |
| Example 1 | 100 | 909 ± 72** |
| Example 19 | 100 | 649 ± 23* |

*,**Significantly different from control, P<0.010 and 0.005, respectively.

EXPERIMENT 2

Augmentation of Concanavalin A-induced immunosuppression

Mice (BALB/c strain, male) were immunized intraperitoneally with $2 \times 10^8$ SRBC. Five days later, the spleen was removed and the number of hemolytic PFC was counted. The compounds of this invention were suspended in 0.3% CMC and orally administered to the mice 24 hours prior to the antigen injection. Concanavalin A (Con A, 50 μg/mouse) was intravenously administered immediately after the oral administration of the compounds.

As shown in Table 6, administration of the compounds of this invention significantly augmented Concanavalin A-induced immunosuppression, and induction of suppressor T cells was observed.

TABLE 6

| Compound | Con A | PFC/spleen ($\times 10^{-2}$) (Mean ± S.E.) | Inhibition (%) | Enhancement (%) |
|---|---|---|---|---|
| Control | — | 562 ± 18 | — | |
| | + | 453 ± 17 | 19.4 | |
| Example 1 | — | 466 ± 10 | 17.1 | |
| (50 mg/kg) | + | 126 ± 14* | 77.6 | 300.0 |
| Example 8 | — | 565 ± 13 | — | |
| (50 mg/kg) | + | 209 ± 12 | 62.8 | 223.9 |

*Significantly different from Con A (30) control, P<0.001.

EXPERIMENT 3

Therapeutic effect on adjuvant arthritis in Lewis rats

Adjuvant arthritis was induced by intradermal injection of heat-killed *Mycobacterium butyricum* cells (0.5 mg/rat) suspended in liquid paraffin into the right hind foot pad of male Lewis rats (n=8). The compounds of this invention suspended in 0.3% CMC solution were orally administered once a day for 7 days during days 10 to 16 after adjuvant injection. Hind paw volume of left foot pad was measured by the water immersion method.

As shown in Table 7, administration of the compounds of this invention significantly reduced the swelling of uninjected (left) hind-paw, and thus, therapeutic effect on adjuvant arthritis was confirmed.

TABLE 7

| Compound | Dose (mg/kg) | Increased left foot volume (ml) | | | (Mean ± S.E.) |
| --- | --- | --- | --- | --- | --- |
| | | Day 17 | Day 21 | Day 24 | Day 28 |
| Control | — | 1.53 ± 0.19 | 1.88 ± 0.16 | 2.09 ± 0.18 | 2.08 ± 0.17 |
| Example 1 | 100 | 0.85 ± 0.20* | 1.17 ± 0.19** | 1.24 ± 0.23* | 1.28 ± 0.22** |
| Example 19 | 20 | 1.27 ± 0.14* | 1.34 ± 0.15* | 1.53 ± 0.18* | 1.59 ± 0.14* |

*,**Significantly different from control, P<0.050 and 0.025, respectively.

EXPERIMENT 4

Therapeutic-effect on adjuvant arthritis in Sprague Dawley rats

Therapeutic effect on adjuvant arthritis of Sprague Dawle (SD) rats (male, n=8) was also done in the same manner as Experiment 3 (except induction dose of *M. butyricum* was 0.6 mg/rat). The compounds of this invention were orally administered once a day for 7 days during days 14–20 after adjuvant injection. The results are shown in Table 8. Treatment of adjuvant arthritis with the compounds of this invention lead to a continuing inhibition of the swelling even after discontinuation of therapy.

TABLE 8

| Compound | Dose (mg/kg) | Increased left foot volume (ml) | | (Mean ± S.E.) |
| --- | --- | --- | --- | --- |
| | | Day 17 | Day 21 | Day 27 |
| Control | — | 1.62 ± 0.26 | 1.86 ± 0.30 | 2.02 ± 0.44 |
| Example 12 | 50 | 1.43 ± 0.30 | 1.61 ± 0.30 | 1.55 ± 0.51 |
| Example 18 | 10 | 1.59 ± 0.40 | 1.98 ± 0.38 | 1.25 ± 0.27 |
| | 50 | 1.17 ± 0.18 | 1.13 ± 0.27 | 1.08 ± 0.27 |
| Example 20 | 10 | 1.54 ± 0.29 | 1.68 ± 0.26 | 1.36 ± 0.25 |
| Example 21 | 50 | 1.54 ± 0.22 | 1.71 ± 0.20 | 1.71 ± 0.38 |
| Control | | 1.66 ± 0.30 | 1.81 ± 0.35 | 1.80 ± 0.32 |
| Example 32 | 10 | 1.25 ± 0.21 | 1.65 ± 0.29 | 1.60 ± 0.32 |
| Example 39 | 10 | 1.02 ± 0.13 | 1.22 ± 0.36 | 0.99 ± 0.35 |

These data indicate that the compounds represented by the general formula (I) can be applied not only to rheumatoid arthritis but also to other autoimmune diseases due to T cells dysfunctions.

What is claimed is:

1. Cyclic anthranilic acid derivatives of the following formula (I),

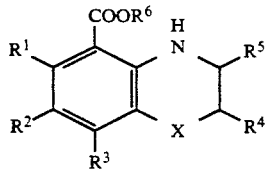

wherein $R^1$, $R^2$ and $R^3$ each independently indicate a hydrogen atom halogen atom, lower alkyl group having 1 to 3 carbon atoms, lower alkoxy group having 1 to 3 carbon atoms, amino group, nitro group, hydroxy group, sulfonamide group, trifluromethyl group, cyano group, carboxyl group, carbamoyl groups, acetyl group, benzoylmethyl group which may be substituted, methylthio group, phenylethynyl group which may be substituted, ethynyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzyl group; wherein said substituents are 1 to 3 members of the group consisting of halogen atom, lower alkyl group, lower alkoxy group and hydroxy group; provided that $R^1$, $R^2$, $R^3$, $R^4$ and $R^5$ are not simultaneously hydrogen; $R^6$ indicates a hydrogen atom, lower alkyl group having 1 to 3 carbon atoms or benzyl group; X indicates an oxygen atom; their acid or alkali salts thereof.

2. An antirheumatoid and immunomodulatory pharmaceutical composition comprising a pharmaceutically acceptable carrier and an effective amount of a compound of the following formula (I),

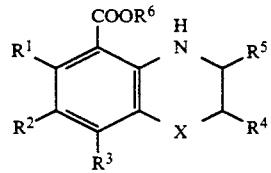

wherein $R^1$, $R^2$ and $R^3$ each independently indicate a hydrogen atom halogen atom, lower alkyl group having 1 to 3 carbon atoms, lower alkoxy group having 1 to 3 carbon atoms, amino group, nitro group, hydroxy group, sulfonamide group, fluoromethyl group, cyano group, carboxyl group, carbamoyl group, acetyl group, benzoylmethyl group which may be substituted, methylthio group, phenylethynyl group which may substituted, ethynyl group which may be substituted, alkanoylamino group having 1 to 3 carbon atoms, benzoylamino group which may be substituted, alkylsulfonylamino group having 1 to 3 carbon atoms or phenylsulfonylamino group which be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzyl group; wherein said substituents are 1 to 3 members of the group consisting of halogen atom, lower alkyl group, lower alkoxy group and hydroxy group; provided that $R^1$, $R^2$, $R^3$, $R^4$ and $R^5$ are not simultaneously hydrogen; $R^6$ indicates a hydrogen atom, lower alkyl group having 1 to 3 carbon atoms or benzyl group; X indicates an oxygen atom; their acid or alkali salts thereof.

* * * * *